United States Patent [19]

Rahman et al.

[11] Patent Number: 5,648,090

[45] Date of Patent: Jul. 15, 1997

[54] LIPOSOME ENCAPSULATED TOXOL AND A METHOD OF USING THE SAME

[75] Inventors: Aquilur Rahman, Gaithersburg, Md.; Rafael Rafaeloff, Tel-Aviv, Israel; Syed Rafat Husain, Gaithersburg, Md.

[73] Assignee: Georgetown University, Washington, D.C.

[21] Appl. No.: 451,258

[22] Filed: May 26, 1995

Related U.S. Application Data

[62] Division of Ser. No. 136,090, Oct. 14, 1993, Pat. No. 5,424,073, which is a continuation of Ser. No. 855,667, Mar. 23, 1992, abandoned.

[51] Int. Cl.$^6$ .................................................. A61K 9/127
[52] U.S. Cl. ............................................................ 424/450
[58] Field of Search ............................................. 424/450

[56] References Cited

U.S. PATENT DOCUMENTS

| | | | |
|---|---|---|---|
| 4,534,899 | 8/1985 | Sears | 544/80 |
| 4,898,735 | 2/1990 | Barenholz | 424/450 |
| 4,952,408 | 8/1990 | Rahman | 514/883 |
| 4,960,790 | 10/1990 | Stella | 514/449 |
| 5,059,591 | 10/1991 | Janoff | 514/31 |
| 5,094,854 | 3/1992 | Ogawa | 424/423 |
| 5,424,073 | 6/1995 | Rahman | 424/450 |

OTHER PUBLICATIONS

Rahman et al., Cancer Research, vol. 42, p. 1817, (1982).

Ostro, American Journal Hosp. Pharm., vol. 46, p. 1579, (1989).

Rosa, Transplant Biochem. Model. Syn. Res., p. 24, (1982).

Primary Examiner—Gollamudi S. Kishore
Attorney, Agent, or Firm—Foley & Lardner

[57] ABSTRACT

Liposomal-encapsulated taxol or an antineoplastic derivative thereof or a mixture thereof is provided which is used to effect a therapeutically enhanced method of treating cancer, and which may be used advantageously in combination with hyperthermia. The liposomes confer enhanced stability and solubility to taxol or derivatives thereof.

11 Claims, 6 Drawing Sheets

LIPOSOME ENCAPSULATED TOXOL AND A METHOD OF USING THE SAME

This application is a division Ser. No. 08/136,090 filed Oct. 14, 1993 now U.S. Pat. No. 5,424,073 which is a continuation Ser. No. 07/855,667, filed Mar. 23, 1992 now abandoned.

BACKGROUND OF THE INVENTION

1. Field of the Invention

The present invention relates to liposome encapsulated taxol and a method of using the same.

2. Description of the Background

Taxol, which is (2aR-(2aα, 4aβ, 6β, 9α(αR*, βS*), 11α, 12α, 12aα, 12bα))-β-(β-(benzoylamino)-α-hydroxybenzenepropanoic acid 6, 12b-bis(acetyloxy)-12-(benzoyloxy)-2a, 3, 4, 4a, 5, 6, 9, 10, 11, 12, 12a, 12b-dodecahydro-4, 11-dihydroxy-4a, 8, 13, 13-tetramethyl-5-oxo-7, 11-methano-14-cyclodeca (3, 4) benz (1, 2-6) oxet-9-yl ester, has the formula (I):

Taxol was first isolated from the bark of the Pacific yew tree, *Taxus breviofolia* Taxaceae and has been shown to exhibit significant antineoplastic activity against the intraperitoneally (i.p.) implanted B16 melanoma, L1210 leukemia, P388 leukemia and the human MX-1 mammary tumor xenograft. More recently, it was determined that taxol exhibits tumor shrinkage in 30 to 40% of women with advanced ovarian tumors. Taxol has also shown considerable promise in the treatment of metastatic breast cancer.

Taxol inhibits normal cellular replication in vitro by promoting microtubule assembly and stabilizing tubulin polymers against depolymerization. Taxol functions as a mitotic spindle poison and is a potent inhibitor of cell replication in vitro. Taxol markedly enhances all aspects of tubulin polymerization, initiation and elongation are more rapid.

As noted in clinical trials, taxol has shown sufficient activity against lymphoma, ovarian and breast cancers.

Due to its limited solubility in water, taxol is prepared and administered in a vehicle containing cremophor EL, a polyoxyethylated castor oil, and ethanol in a 50:50 (vol/vol) ratio. This solution is further diluted 1:10 in saline before administration to humans. In clinical trials, a consistent problem of anaphylactoid reaction, dyspnea, hypertension and flushing have been encountered. The cardiac toxicity of taxol is treatment limiting and because of this the patient has to be hospitalized for continuous infusion of the drug.

In addition, the stability of taxol once diluted in saline solution is quite low. The drug degrades within 24 hours and hence handling of dosage for the patients becomes very difficult. In addition, the drug precipitates from dilution and hence an on-line filter is utilized for the infusion of drug to the patients.

Attempts to prevent taxol cardiotoxicity and anaphylactoid reaction have included reliance on pretreatment of patients with antihistamine and corticosteroids, and by prolonging the infusion time from six to twenty four hours. Even with these manipulations, patients suffer from serious toxicities which are often fatal.

Further, taxol has conventionally been obtained from Pacific yew trees in forests of the Pacific Northwest, requiring the sacrifice of about six trees to obtain a sufficient quantity of drug to treat one patient. Although it was recently announced that taxol could be produced synthetically, see *The Wall Street Journal*, Mar. 18, 1992, the yield is necessarily small due to the large number of steps involved in the synthesis.

Thus, even if improved syntheses of taxol could be devised, a number of drawbacks inherent in taxol use remain.

Thus, a need exists for a means by which the above drawbacks may be avoided or their impact minimized.

SUMMARY OF THE INVENTION

Accordingly, it is an object of the present invention to provide liposomal-encapsulated taxol, which minimizes the above drawbacks.

It is also an object of the present invention to provide a method for treating cancer in mammals.

Further, it is a particular object of the present invention to provide a method for treating lymphoma, breast, ovarian, lung and colon cancer in mammals.

Accordingly, the above objects and others are provided by liposomal-encapsulated taxol and antineoplastic derivatives thereof.

DETAILED DESCRIPTION OF THE PREFERRED EMBODIMENTS

The present invention relates generally to liposome-encapsulated taxol and methods of using the same. Generally, any method of using taxol with a conventional therapeutic objective may be practiced in accordance with the present invention with surprisingly enhanced results.

In part, the present invention provides a delivery system for taxol to mammalian host which is characterized by 1) avoidance of solubility problems of taxol, 2) improved taxol stability, 3) avoidance of anaphylactoid reactions and cardiotoxicity, 4) ability to administer taxol as a bolus or short infusion rather than extended (24-hour) infusion of free taxol, 5) increased therapeutic efficacy of taxol, and 6) modulation of multidrug resistance in cancer cells.

As used herein, the term "liposome" means a closed structure composed of lipid bilayers surrounding an internal aqueous space.

Further, as used herein, the phrase "taxol as an antineoplastic derivative thereof" means taxol or any derivative of taxol which is or may be used in cancer chemotherapy due to its antineoplastic properties. It is particularly noted that although taxol is believed to function as an antineoplastic compound by promoting microtubule assembly and stabilizing tubulin polymers against depolymerization, the derivatives of the present invention are not limited to those which function by any particular mechanism.

For example, in addition to taxol, derivatives such as taxasm or others mentioned in synthesis and Anticancer Activity of Taxol derivatives D.G.I. Kingston et al, Studies in Organic Chemistry, volume 26, entitled "New Trends in Natural Products Chemistry"1986, Atta-ur-Rahman, P.W. le Quesue, Eds. (Elvesier, Amsterdam 1986), pp. 219–235 are explicitly included within the present invention. Further, the literature excerpt mentioned above is incorporated herein in the entirety.

Generally, in accordance with the present invention, taxol or a derivative thereof is dissolved in a suitable solvent. As a solvent, any non-polar or slightly polar solvent may be used, such as ethanol, methanol, chloroform or acetone. Then, cardiolipin is dissolved in a suitable solvent as described for taxol and the solutions are mixed.

Then, lipid-forming material is dissolved in a suitable solvent, which is generally a low polarity solvent such as chloroform, or a non-polar solvent, such as n-hexane the solvent mixture from above and the solution containing the lipid-forming material are mixed, and the solvents are removed to afford a thin, dry film of lipid and drug.

Liposomes are then formed by adding saline solution thereto. Thereafter, multi-lamellar liposomes may be formed by mixing the liposomes, for example, by vortexing.

Generally, the liposomes may be neutral, negative or positive liposomes. For example, positive liposomes may be formed from a solution containing phosphatidyl choline, cholesterol and staryl amine. Negative liposomes may be formed, for example, from solutions containing phosphatidyl choline, cholesterol and phosphatidyl serine.

Furthermore, is mixing the saline solution with the thin, dry film of lipid and drug, any form of dispersion may be used provided that it strongly homogenizes the mixture. For example, such homogenization may be effected by using a vortex, magnetic stirrer and/or sonication.

The cardiolipin used in accordance with the present invention may be obtained from either a natural or synthetic source as is known to those skilled in the art.

Having described the present invention, reference will now be made to certain examples which are provided solely for purposes of illustration and which are not intended to be limitative.

EXAMPLE 1

To 2.93 µM of taxol dissolved in chloroform 2.81 µM of cardiolipin in ethanol was added. To this mixture, 14.16 µM of phosphatidyl choline dissolved in hexane and 9.83 µM cholesterol in chloroform was added. The mixture was stirred gently and then solvents were evaporated under vacuum at below 30° C. A thin dry film of lipid and drug was formed. Liposomes were formed when 2.5 ml saline solution was added. The flasks were vortexed for ½ hour to provide multilamellar liposomes. These liposomes were then sonicated for ½ hour in a Heat System Cup horn sonicator which provided small unilamellar liposomes. The liposomes were then dialyzed against 1 liter saline solution for 24 hours. After the completion of dialysis, an aliquot of liposomes was dissolved in methanol and analyzed by high pressure liquid chromatography (HPLC). The encapsulation efficiency of taxol in liposomes was more than 95% of the initial input dose. The taxol concentration in these liposomes was 0.95 mg/ml.

EXAMPLE 2

In this preparation same experimental conditions were utilized except the quantities of drug and lipids were varied. For this preparation, the following concentrations were used: Taxol 5.86 µM, cardiolipin 5.62 µM, phosphatidyl choline 28.18 µM and cholesterol 19.38 µM. The solvents were then evaporated under vacuum and the dried lipids and drug layers were dispersed with 5 ml of 7% Trehalose-saline solution, hydrated, vortexed and sonicated. The liposomes were then dialyzed for 24 hours and the percent encapsulation of taxol in liposomes was more than 94% as assayed in HPLC.

EXAMPLE 3

To explore the potential use of taxol liposomes in hyperthermia, taxol was encapsulated in liposomes by using 2.58 µM of the drug, 15.26 µM of dipalmitoyl phosphatidyl choline and 8.79 µM cholesterol. The drug and lipid mixture was evaporated under vacuum and resuspended in 2.5 ml of saline. The remainder of the process was similar as described above. The taxol encapsulation efficiency was higher than 95%.

EXAMPLE 4

In this preparation of liposomes, cardiolipin was substituted with phosphatidyl serine to form taxol liposomes. In this case 2.11 µM taxol, 2.10 µM of phosphatidyl serine, 10.77 µM phosphatidyl choline and 7.24 µM cholesterol were used. The whole process was performed as described earlier and the liposomes were dialyzed extensively overnight and then the drug was assayed by HPLC. The percent encapsulation of taxol was found to be more than 95%.

Stability Studies

Figure 1:
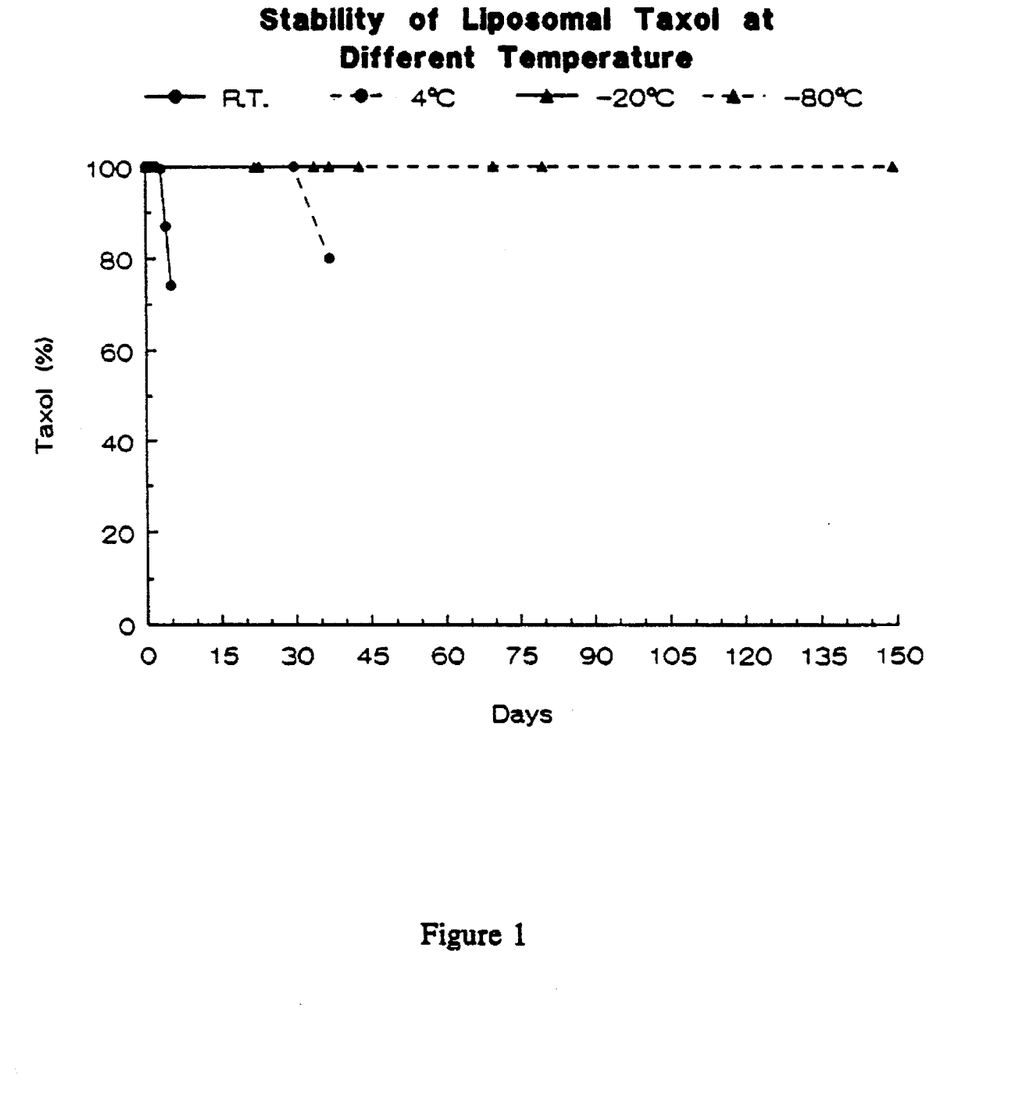
FIG. 1 illustrates the stability of liposomal taxol at different temperatures.

The taxol liposomes were prepared as usual using cardiolipin, phosphatidyl choline and cholesterol. An aliquot of these liposomes was placed at room temperature, and refrigeration temperature (4° C.). As shown in the FIG. 1, the taxol liposomes at room temperature were stable for four days. On the contrary, the free taxol of 0.6 mg/ml concentration in saline degrades within 3 hours. The liposomal taxol at refrigeration temperature were stable for 1 month.

In another set of experiments, taxol liposomes were prepared in the usual way but instead of using saline, 7% trehalose-saline (a diglucose sugar) was used to resuspend the liposomes. Aliquots of these liposomes were placed at −20° C. and at −80° C. At −20° C., the taxol liposomes were also stable for 1 month as determined by HPLC. The experiment was terminated at this time. The liposomes with 7% trehalose were frozen at −80° C. for 5 months. Intermittently, the liposomes were thawed and frozen again. This process was repeated several times. At the end of 5 months, the liposomes were dialyzed against 7% trehalose solution and the content of taxol in dialyzed liposomes was measured by HPLC, and was found to be 93% of the initial concentration of taxol in those liposomes. This experiment demonstrates that taxol liposomes with trehalose as an excipient can be effective means of storing the liposomes frozen and be effectively used for clinical and therapeutic application after thawing the liposomes.

Toxicity Evaluation of Taxol Liposomes

Figure 2:
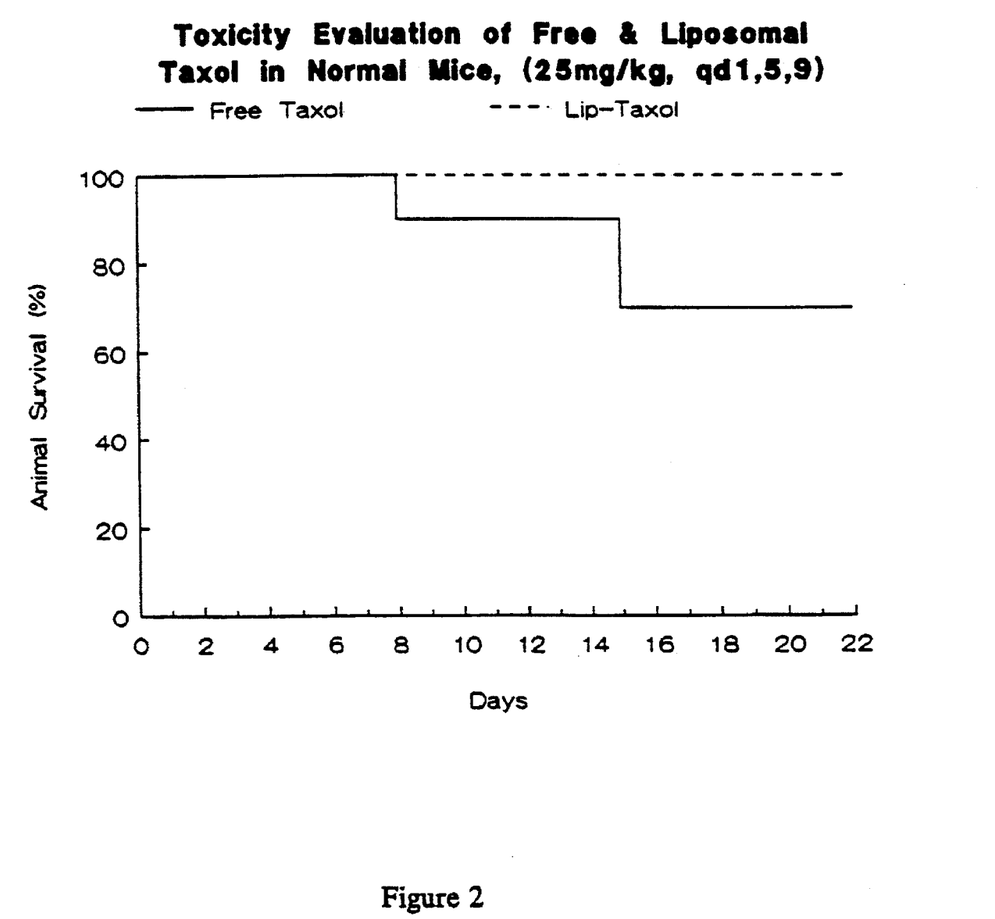
FIG. 2 illustrates a toxicity evaluation of free and liposomal taxol in normal mice.

Male $CD_2F_1$ mice weighing 22–25 gm were used in this study. Free taxol which is formulated in cremophor EL was diluted with saline to provide a concentration of 1.25 mg/mol. Taxol liposomes were prepared using cardiolipin, phosphatidyl choline, and cholesterol. The final taxol concentration in liposomes was 1.25 mg/ml. Ten mice in each group were injected with free taxol or liposomal encapsulated taxol at a dose of 25 mg/kg i.v. This is the highest dose of free taxol which can be injected into the mice because of the solubility limitations and alcohol content. The same doses were repeated on mice at day 5 and 9. No further injections could be given in mice which received free taxol because of the sclerosis of the vein. As shown in FIG. 2 by day 12, three mice in the free taxol group died because of toxicity whereas no toxicity or mortality was observed in mice which were injected with taxol encapsulated in liposomes.

Therapeutic Evaluation of Free Taxol and Liposome Encapsulated Taxol in Mice Bearing L1210 Leukemia The L1210 murine leukemia cancer was propagated in female DBA/2 mice. For therapeutic studies, $CD_2F_1$ mice were implanted i.p. with $1 \times 10^5$ cells of L1210 leukemia and twenty four hours after tumor implantation, they were injected with free taxol or taxol encapsulated in liposomes. All the mice received dose of 6 mg/kg i.p. on days 1 to 5. Tumor bearing control mice were injected with normal saline in a same volume as experimental mice. All injections were made at 2% body weight basis. Mice were weighed on days of injection, doses of drugs were calculated on body weight basis and the survival time was recorded in days.

Table 1 shows the effectiveness of free taxol and taxol encapsulated in liposomes on the survival of mice bearing L1210 tumor. Mice when injected with free taxol at a dose of 6 mg/kg i.p. from day 1–5 exhibited a T/C of 135% (treated vs control). The same dose of taxol when injected as the liposome encapsulated drug produced a T/C of 178% demonstrating that survival of tumor bearing mice is substantially enhanced when treated with this modality of treatment. These studies demonstrate that not only the toxicities of taxol are reduced when encapsulated in liposomes but this encapsulation also provides a higher therapeutic ratio in tumor bearing mice.

Cytotoxicity Evaluation of Free Taxol and Liposome Encapsulated Taxol on HL-60 Human Leukemia Cells HL-60 promyelocytic leukemia cells were grown in tissue culture in RPMI-1640 medium supplemented with 10% fetal bovine serum. All cultures were maintained in plastic tissue culture flasks and kept in an incubator at 37° C. in humidified air containing 5% $CO_2$.

Figure 3:
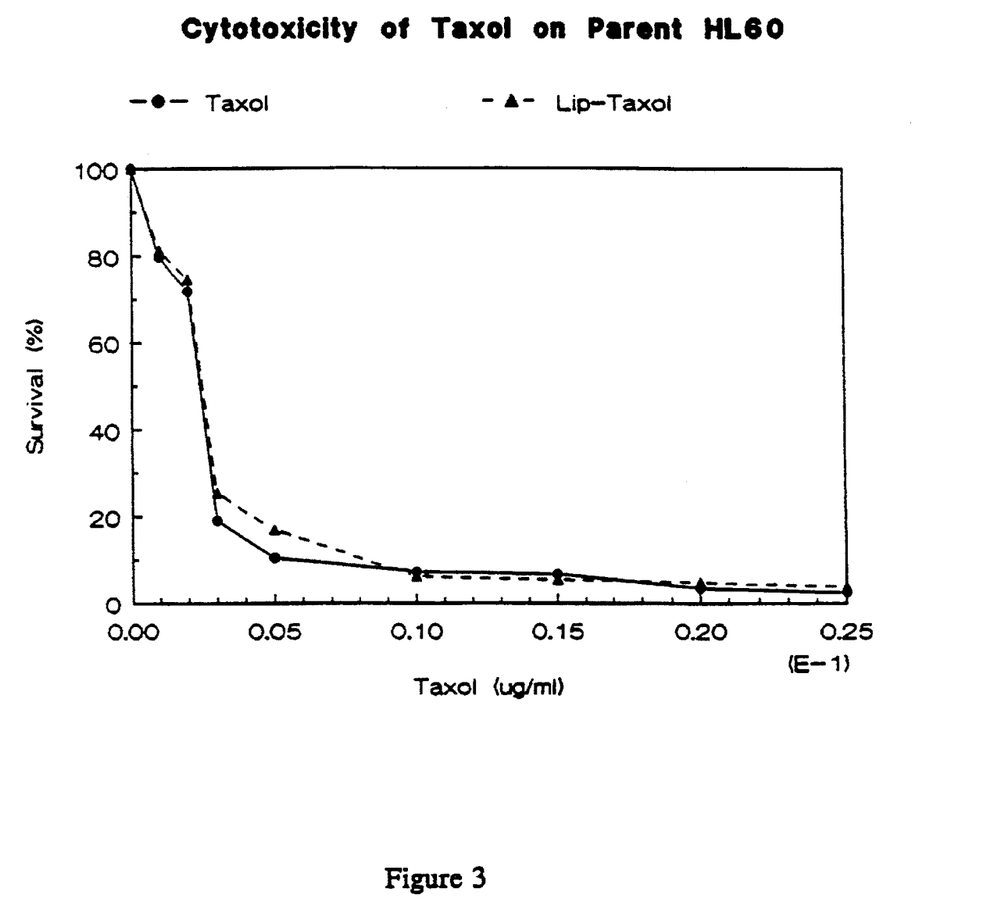
FIG. 3 illustrates cytotoxicity of taxol on parent HL leukemia cells.

The growth inhibition method was used to determine the cytotoxicity of free taxol and liposomal encapsulated taxol. For these experiments, $1 \times 10^5$ cells in exponential growth phase were plated into 25 cm$^2$ flasks. They were then exposed to varying concentration of free taxol and liposomal taxol for 72 hours at 37° C. Cells were counted in a hemocytometer and viability was determined by trypan blue exclusion. The cell survival was compared to the control cells and $IC_{50}$ (inhibitory concentration for 50% of the cells) values for each drug was determined. As shown in FIG. 3, the $IC_{50}$ values for free taxol were 0.0025 µg/ml and the same $IC_{50}$ values for taxol encapsulated in liposomes were obtained. These experiments demonstrate that free taxol and liposomal taxol are as equivalent in their effectiveness to produce cytotoxicity to the HL-60 leukemia cells.

Intracellular Accumulation of Free Taxol and Liposome Encapsulated Taxol

Figure 4:
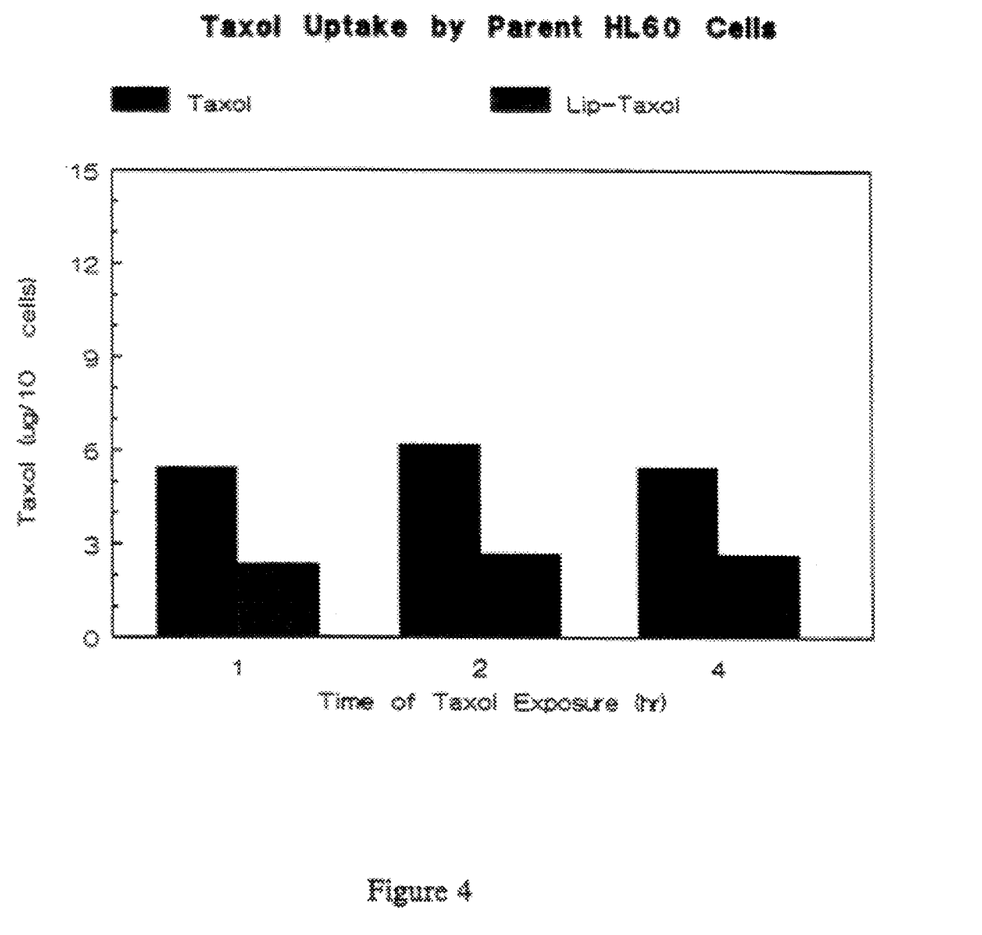
FIG. 4 illustrates taxol uptake by parent HL 60 cells.

The cellular content of taxol was determined by high pressure liquid chromatography (HPLC). Briefly, exponentially growing cells were incubated in 100 mm petri dishes with drug containing medium at 37° C. The cells were treated for 1 to 4 hours with either free taxol or liposomal taxol at 10 µg/ml drug concentration, and were then centrifuged and rinsed twice with PBS. The cell pellets were suspended in 0.5 ml of 2% SDS solution and then sonicated for 5 minutes in a cup-horn sonicator. The cell homogenate was extracted with 2 ml of methanol. An aliquot of this solution was injected into HPLC for quantitative determination of taxol. As shown in FIG. 4, the cellular concentration of drug when exposed with free taxol was achieved to a maximum level at 1 hour, the value being 5.18 µg/$10^7$ cells. The same taxol concentration was observed at 2 and 4 hours of drug exposure. However, with liposomal taxol the cellular dry concentration was consistently lower than observed with free taxol. At 1 hour exposure, the cellular concentration of taxol was 2.3 µg/$10^7$ cells and this value was more or less similar to 2 and 4 hour exposure with liposomal taxol. This experiment demonstrates that even if the uptake of liposome encapsulated drug is less in HL-60 cells, the cytotoxicity is similar with either modality of treatment.

Modulation of Multidrug Resistance in Cancer Cells by Liposomal Taxol

Resistance of tumor cells to chemotherapy is one of the major reasons for treatment failures in cancer patients. Over the last ten years, a major emphasis has been to define the mechanisms of tumor resistance to chemotherapy. This tumor resistance has been shown to be the result of amplified expression of multidrug resistance gene in cancer cells. The product of this multidrug resistance gene, p-glycoprotein of 170,000 daltons, functions as an efflux pump and confers resistance to cytotoxic action of structurally unrelated cancer chemotherapeutic drugs by producing lower intracellular levels of drugs.

Our studies demonstrate that liposome encapsulated taxol has significant capacity to overcome multidrug resistance. These studies were performed in HL 60/VCR cells which are promyelocytic human leukemia cells and are derived from parent HL-60 cells and are made resistant to vincristine demonstrating multidrug resistance phenotype. The HL-60 VCR cells were grown in media at 37° C. with 5% CO.

An accurately known number of cells were placed in tissue culture flasks and were treated with varying concentrations of free taxol, taxol encapsulated in liposomes and blank liposomes representing the same concentration of lipids as used for taxol. After 72 hours of incubation, cells in each flask were counted by hemocytometer and viability was determined by trypan blue exclusion. Percent survival of treated cells was determined relative to untreated control. Cytotoxic activity was expressed as $IC_{50}$ which was defined as the concentration of drug resulting 50% survival of the cells compared to control.

Figure 5:
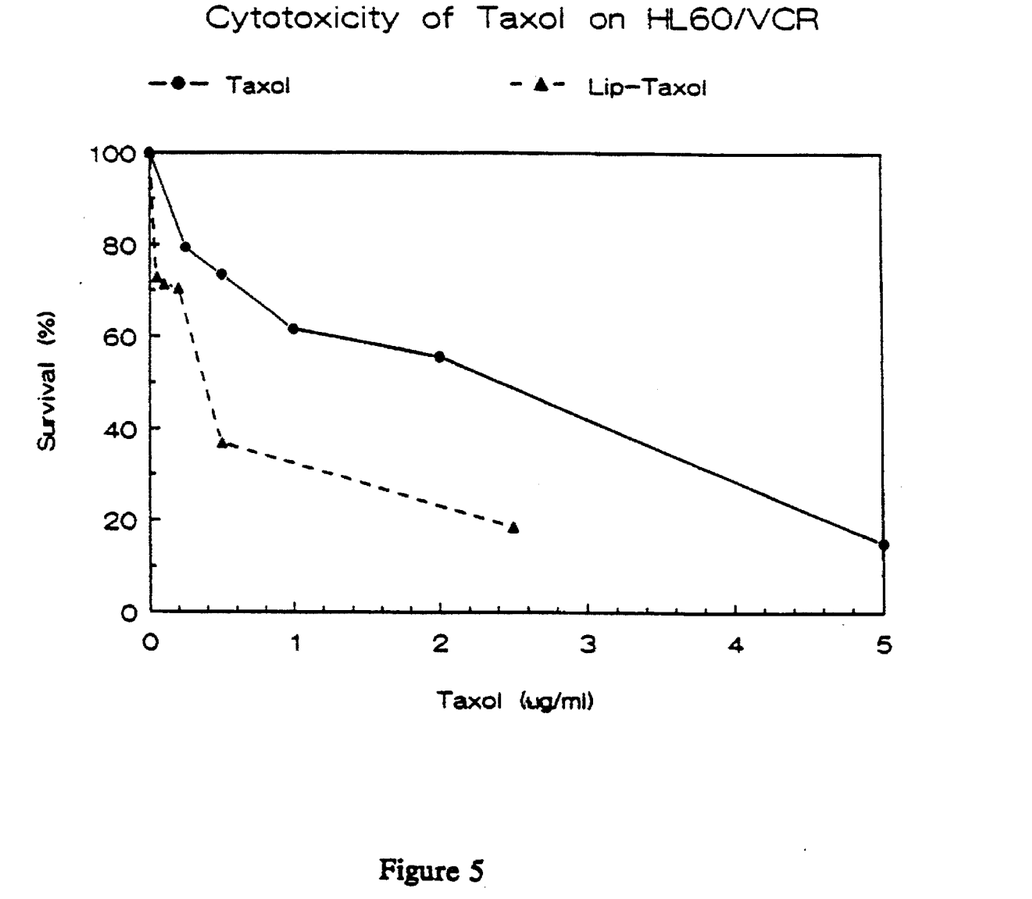
FIG. 5 illustrates cytotoxicity of taxol on HL 60/VCR cells.

The survival curves of HL-60/VCR cells after exposure to free taxol and liposome encapsulated taxol are presented in FIG. 5. The $IC_{50}$ for free taxol in HL-60/VCR is 2.43 µg/ml demonstrating this cell line is 1280 fold resistant than the parent HL-60 cell line. However, the $IC_{50}$ for liposomal taxol is only 0.37 µg/ml. This demonstrates that liposomal taxol sensitizes 7 fold the HL-60/VCR as compared to free taxol. Hence, it is apparent that liposome encapsulated taxol modulates drug resistance in the multidrug resistance phonotype which potentially would be a major advantage in a clinical situation where a large population of the patients fail to respond to chemotherapy because of multidrug resistance.

Intracellular Taxol Accumulation in Multidrug Resistance Cells

The cellular content of taxol was determined by High Pressure Liquid Chromatography. In brief, the multidrug resistance HL-60/VCR exponential growth phase cells were incubated in 100 mm petri dishes with drug containing medium at 37° C. containing either free taxol or taxol encapsulated in liposomes. The cells were treated for 1 to 4 hours with either of the drug and were then centrifuged and rinsed twice with PBS. The cells were suspended in cold PBS and counted, and centrifuged again. The cell pellets were suspended in 0.5 ml of 2% SDS solution and then sonicated for 5 minutes in a cup-horn sonicator (Heat Systems, Farmingdate, N.Y.). Resulting cell homogenate was extracted with 4 ml of methanol, vortexed for 1 minute and centrifuged for 20 minutes at 3000 rpm. The samples were read by using HPLC. The concentration of drug in 10 cells was calculated using a standard calibration curve for drug spiked cells and were then treated similarly.

Figure 6:
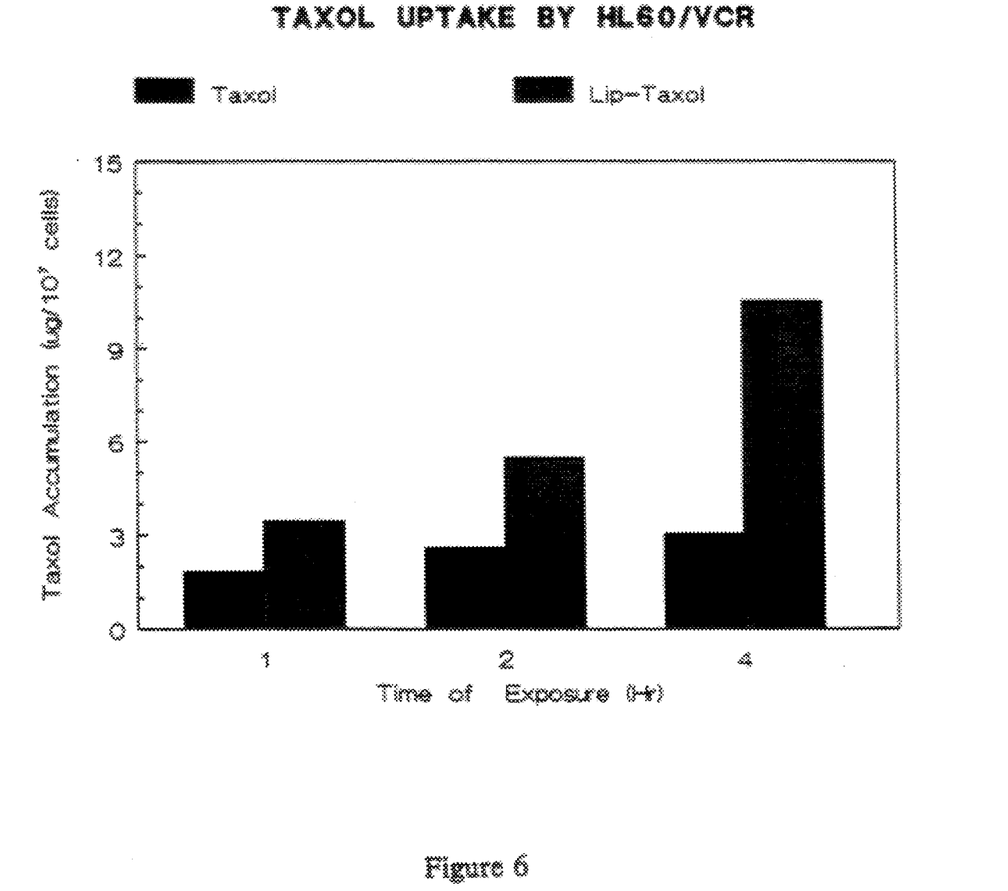
FIG. 6 illustrates taxol uptake by HL 60/VCR cells.

FIG. 6 illustrates the accumulation of taxol in HL-60/VCR resistant phenotype cells following treatment with 10 µg/ml of free drug and liposomal encapsulated taxol for a period of 1 to 4 hours. The resistant HL-60/VCR cells demonstrated maximal uptake of liposomal encapsulated taxol and with time of exposure the intracellular drug accumulation correspondingly increased. By 4 hours, the drug accumulation was 10.54 $µg/10_{77}$ cells with liposomal taxol whereas with free taxol it was only 3.04 $µg/10_7$ cells showing a threefold decrease in cellular uptake. The same relationship was observed at earlier time of cellular exposure and a difference of twofold drug concentration between free taxol and liposomal taxol was evident. These data suggest that modulation of drug resistance in HL-60/VCR cells can be partially explained by enhanced cellular drug uptake with liposomal encapsulated taxol. The enhanced cellular uptake and effective modulation of multidrug resistance in HL-60/VCR cells by liposomal encapsulated taxol demonstrates this modality of treatment can be of high clinical advantage for patients who have failed cancer chemotherapy previously. Overall, this modality of treatment is more effective than free taxol and can be successfully applied in cancer patients.

In accordance with the present invention, the present invention may be used to treat any mammal, such as a cow, horse, pig, dog or cat. However, it is particularly preferred if the mammal treated is human.

As referred to above, Table 1 is provided hereinbelow.

TABLE

Therapeutic Evaluation-of Free Taxol and Liposome Encapsulated Taxol Against L1210 Leukemia

| Dose | | % T/C |
|---|---|---|
| 6 mg/kg | Free Taxol | 135 |
| 6 mg/kg | Lipsomal-encapsulated Taxol | 178 |

Generally, taxol, for example, may be obtained by isolation as a natural product from the bark of the Pacific Yew tree. See M. C. Wani et al, *J. Amer. Chem. Soc.*, vol. 93, 2325 (1971). However, taxol or an antineoplastic derivative thereof may be synthesized in the laboratory. See J.-N. Denis et al, *J. Amer. Chem. Soc.*, vol. 110, pp. 5917–5919 (1988).

Furthermore, taxol and the derivatives thereof in accordance with the present invention may be used to treat any form of mammalian cancer, particular those compounds which function by promoting the assembly of microtubules and which prohibit the tubulin disassembly process. However, the present compounds are particularly advantageous in treating mammalian lymphoma, ovarian, breast, lung and colon cancer, more particularly those of humans.

In accordance with the present invention, the liposomal-encapsulated taxol or antineoplastic derivatives thereof are generally administered intravenously or intraperitoneally to the mammal. Further, the present compound or compounds are generally administered in the amount of about 50–250 mg active compound/$m^2$ of mammalian host surface area.

For a human, for example, of about 70 kg body weight, from about 0.5–5.0 mg active compound per kg of body weight is administered. Preferably, about 1.0–3.0 mg of active compound per kg of body weight is administered.

Thus, the present invention also provides methods of treating various mammalian cancers, particularly human cancers.

Moreover, the present invention also provides a method of modulating multidrug resistance in cancer cells which are subjected to chemotherapy. In accordance with this aspect of the present invention, it has been discovered that by using the liposomal compositions of the present invention, it is possible to reduce the tendency of cancer cells subjected to chemotherapy to develop resistance to the chemotherapeutic agents used for chemotherapy.

In particular, the present liposomal compositions not only reduce the tendency of cancer cells subjected to chemotherapy with taxol and derivatives thereof to develop resistance thereto, but the present compositions also reduce the tendency of cancer cells to develop resistance to other agents used for chemotherapy, such as anthracycline glycosides, for example.

Furthermore, in accordance with the present invention, it has been discovered that the present liposome compositions can be administered intravenously or intraperitoneally to an isolated portion of a mammalian body particularly a human body, such as an arm or leg, or in the case of a human, a hand. Then, that portion of the mammalian body may be subjected to a hyperthermia treatment. Hyperthermia treatments are well known to those in the art. Quite surprisingly, it has been discovered that upon effecting hyperthermia treatment the administered liposomes melt to provide a highly localized dosage of taxol or derivative thereof. Of course, the dosage administered will depend upon the body weight of the mammal being treated and the judgment of the treating physician. In accordance with this aspect of the present invention, the hyperthermia treatment may be administered before, contemporaneously or after administration of the active ingredient or ingredients, and the liposomes may either be administered locally or generally throughout the body.

Having described the present invention it will be apparent that one skilled in the art may make many changes and modifications to the above-described embodiments without departing from the spirit and scope of the present invention.

What is claimed as new and desired to be secured by Letters Patent of the United States is:

1. A method of modulating multidrug resistance in cancer cells in a mammalian host, comprising administering to said host a pharmaceutical composition comprising:

(i) a therapeutically effective number of liposomes comprising a liposome-forming material, cardiolipin, and an agent selected from the group consisting of taxol, an antineoplastic derivative of taxol, or a mixture thereof; and (ii) a pharmaceutically acceptable excipient.

2. The method of claim 1, wherein said mammalian host is a human.

3. The method of claim 1, wherein said pharmaceutical composition further comprises a chemotherapeutic agent other than taxol or an antineoplastic derivative of taxol.

4. The method of claim 3, wherein said chemotherapeutic agent is an anthracycline glycoside.

5. The method of claim 1, wherein said antineoplastic derivative of taxol is taxotere.

6. The method of claim 1, wherein said liposome-forming material is at least one of the lipids selected from the group consisting of phosphatidyl choline, cholesterol, dipalmitoyl phosphatidyl choline and phosphatidyl serine.

7. The method of claim 1, wherein said cardiolipin is selected from the group consisting of natural cardiolipin and synthetic cardiolipin.

8. The method of claim 1, wherein said liposome bears a negative charge.

9. The method of claim 1, wherein said liposome bears a positive charge.

10. The method of claim 1, wherein said liposome is neutral.

11. The method of claim 1, wherein said liposomes are a mixture of multilamellar vesicles and unilamellar vesicles.

* * * * *

UNITED STATES PATENT AND TRADEMARK OFFICE
CERTIFICATE OF CORRECTION

PATENT NO.  :   5,648,090
DATED       :   July 15, 1997
INVENTOR(S) :   RAHMAN et al.

It is certified that error appears in the above-indentified patent and that said Letters Patent is hereby corrected as shown below:

On the title page, item [54] and col. 1, line 1, delete "TOXOL" and substitute therefor --TAXOL--.

Signed and Sealed this

Seventh Day of October, 1997

*Attest:*

BRUCE LEHMAN

*Attesting Officer*     Commissioner of Patents and Trademarks